United States Patent [19]
Ndondo-Lay et al.

[11] Patent Number: 5,549,556
[45] Date of Patent: Aug. 27, 1996

[54] RAPID EXCHANGE CATHETER WITH EXTERNAL WIRE LUMEN

[75] Inventors: Robert Ndondo-Lay; Garry E. Rupp, both of San Diego, Calif.

[73] Assignee: Medtronic, Inc., Minneapolis, Minn.

[21] Appl. No.: 979,094

[22] Filed: Nov. 19, 1992

[51] Int. Cl.⁶ .............................................. A61M 29/00
[52] U.S. Cl. .......................... 604/102; 604/96; 606/194
[58] Field of Search .................... 606/191, 192, 606/194; 604/96, 280, 282

[56] References Cited

U.S. PATENT DOCUMENTS

| | | |
|---|---|---|
| 4,576,142 | 3/1986 | Schiff . |
| 4,723,936 | 2/1988 | Buchbinder . |
| 4,748,982 | 6/1988 | Horzewski . |
| 4,762,129 | 8/1988 | Bonzel . |
| 4,787,399 | 11/1988 | Bonello et al. ........................ 128/772 |
| 4,824,435 | 4/1989 | Giesy . |
| 4,917,666 | 4/1990 | Solar . |
| 4,983,167 | 1/1991 | Sahota . |
| 4,988,356 | 1/1991 | Crittenden . |
| 5,019,042 | 5/1991 | Sahota . |
| 5,024,234 | 6/1991 | Leary . |
| 5,040,548 | 8/1991 | Yock . |
| 5,046,497 | 9/1991 | Millar . |
| 5,054,492 | 10/1991 | Scribner . |
| 5,057,120 | 10/1991 | Farcot ..................... 606/194 |
| 5,061,273 | 10/1991 | Yock . |
| 5,071,406 | 12/1991 | Jang . |
| 5,087,247 | 2/1992 | Horn . |
| 5,102,403 | 4/1992 | Alt ........................................ 604/280 |
| 5,108,366 | 4/1992 | Schatz ................................... 604/55 |
| 5,135,535 | 8/1992 | Kramer . |
| 5,141,494 | 8/1992 | Danforth . |
| 5,154,725 | 10/1992 | Leopold . |
| 5,156,594 | 10/1992 | Keith ..................................... 604/96 |
| 5,180,367 | 1/1993 | Kontos et al. ........................ 604/101 |
| 5,257,974 | 11/1993 | Cox ....................................... 604/96 |

*Primary Examiner*—Corrine M. McDermott
*Attorney, Agent, or Firm*—Dianne M. F. Plunkett; Harold R. Patton

[57] ABSTRACT

A catheter formed of an elongated shaft with a dilatation balloon at the distal end includes a guide wire lumen external to the balloon. The guidewire lumen extends from the distal tip of the catheter to a proximal port distal from the proximal end of the catheter. The shaft is formed of a proximal hypotube and a distal spring coil. In some embodiments, the wire lumen extends the full length of the catheter and includes apertures for drug delivery or perfusion. A core wire is included to enhance the pushability of the catheter and support the balloon.

5 Claims, 5 Drawing Sheets

RAPID EXCHANGE CATHETER WITH EXTERNAL WIRE LUMEN

BACKGROUND OF THE INVENTION

1. Field of the Invention

The present invention relates to over-the-wire catheters and particularly, to rapid exchange and perfusion catheters.

2. Description of the Prior Art

This description of art is not intended to constitute an admission that any patent, publication or other information referred to is "prior art" with respect to this invention, unless specifically designated as such. In addition, this section should not be construed to mean that a search has been made or that no other pertinent information as defined in 37 C.F.R. §1.56 exists.

The technique of eliminating a vascular stenosis by dilating a balloon on a catheter placed within the stenosis was developed by Dr. Andreas Gruntzig. The first marketable catheters for angioplasty were "fixed wire" catheters, in which a core or guide wire was fixed within the catheter to stiffen it so that it could be pushed into position in the vascular system.

Dr. John Simpson and Dr. Edward Robert subsequently developed an "over-the-wire" catheter in which a guidewire was slidably placed within a lumen of the catheter. The guidewire lumen passed from the distal end of the catheter through the balloon to the proximal end of the catheter. This system provided reasonably easy placement of the catheter because the small, flexible guidewire was first positioned beyond the stenosis and the catheter was then slid into place over it. Such over-the-wire catheters are generally coaxial (the guidewire lumen is centered within the inflation lumen) or biaxial or bilumen (the guidewire lumen is parallel to the inflation lumen). Biaxial versions generally slide better over the guidewire than coaxial versions.

More recently, "rapid exchange" catheters have been developed with shorter guidewire lumens passing from the distal end of the catheter through the balloon and opening to the exterior of the catheter somewhere proximal to the balloon; they make catheter exchange over the guidewire easier to accomplish.

Various versions of rapid exchange catheters, either coaxial or biaxial, are shown in the following patents: U.S. Pat. No. 4,762,129 issued to Bonzel, U.S. Pat. Nos. 5,040,548 and 5,061,273 issued to Yock, U.S. Pat. No. 4,748,982 issued to Horzewski, et al., U.S. Pat. No. 4,988,356 issued to Crittenden and U.S. Pat. No. 5,135,532 issued to Kramer. In the Horzewski and Crittenden device, the guidewire lumen contains a slit extending its length (except where it passes through the balloon) so that the guidewire can be removed from the lumen through the slit at a point immediately proximal to the balloon. Examples of rapid exchange catheters on the market are ACS' Alpha™ catheter, ACS' RX™ catheter, Schneider's Piccolino™ and SciMed's Express™ catheter.

Although the above catheters have significantly improved and streamlined the angioplasty process, they still leave room for improvement. For example, visualizing the location of the catheter and the guidewire during fluoroscopy is critical during the process of dilatation in order to properly place the guidewire initially, and in order to place and hold the balloon within the stenosis. As a result, the balloon or adjacent areas of the catheter generally possess a marker band visible under fluoroscopy. The guidewire itself, usually made of stainless steel, is visible under fluoroscopy. However, in the above catheters, because a guidewire lumen surrounds the guidewire, and the balloon (as well as the shaft in the case of a coaxial catheter) surrounds the guidewire lumen, the guidewire is not as visible as might be desired.

In addition, plaque buildup in the vessel is usually disposed on one side or another of the vessel wall rather than evenly located around the entire circumference of the wall. In all of the above catheters, the balloon is symmetrically disposed around the guidewire lumen so that it cannot be optimally placed with respect to the plaque build-up. Although catheters with asymmetric balloons have been disclosed, those such as that in Schiff, U.S. Pat. No. 4,576,142, are intra-aortic balloon catheters with fixed-wire systems, or have multiple balloons with internal lumens, such as that in Jang, U.S. Pat. No. 5,071,406.

Catheters have been disclosed having no guide wire lumen at all, at least in the region of the balloon, the guide wire running exterior and parallel to the balloon in use. See, for example, U.S. Pat. No. 5,141,494 issued to Danforth, et al., U.S. Pat. No. 5,046,497 to Millar, and U.S. Pat. No. 4,824,435 to Giesy. A rapid exchange catheter having a guidewire without a lumen parallel to the balloon is also disclosed in U.S. patent application Ser. No. 07/859,769 assigned to the assignee of the present invention. However, it may be difficult to back-load the guidewire into some of these catheters and it is possible that the naked guidewire will dislodge plaque which it encounters, causing possible serious problems in the dilatation process.

Because inflation of the balloon blocks blood flow during dilatation, long dilatation times are usually precluded by dilatation procedures. However, U.S. Pat. Nos. 4,983,167 and 5,019,042 to Sahota and U.S. Pat. No. 5,087,247 to Horn disclose auto-perfusion catheters in which blood is allowed to flow past the balloon even while it is inflated, allowing much longer inflation times. In some cases, apertures in the guidewire lumen passing through the balloon allow blood to circulate through the system while the catheter is in use; in others, the balloon is shaped to define a longitudinal channel through which the blood flows.

In the Sahota patents, there is disclosed a fixed wire catheter having a wire-receiving lumen adjacent to the inflation lumen proximal to the balloon. The lumen receives a wire which can be extended through the stenosis, if needed, after dilation to prevent closure. However, the naked wire still runs past the balloon through the occlusion to directly encounter the stenosis.

Finally, in order to handle well, a catheter has to be sufficiently "pushable" to be pushed into place into the vascular system. At the same time, it requires flexibility so it can be turned through the tortuous vascular system without kinking. Some catheters, such as the present assignee's 14K™ catheter and Thruflex® catheter (shown in U.S. Pat. No. 4,917,666) are over-the-wire catheters having spring coil lumens to improve the pushability of the catheter. At the same time, the spring coil is flexible laterally, with minimized kinking. In the present assignee's Gold X™ catheter, a coaxial rapid exchange catheter shown in U.S. patent application Ser. No. 07/919,672 filed Jul. 27, 1992, the outer lumen is similarly made of a spring coil, with a core wire extending through a portion of the coil for added pushability. In the present assignee's Omniflex™ catheter (shown generally in U.S. Pat. No. 4,723,936) as sold, a proximal hypotube about 1½ inches long improves the handling of the catheter, which is otherwise formed of a spring coil.

Other rapid exchange catheters having high pushability are SciMed's Express™ catheter, shown in PCT patent application Publication No. WO 92/03178, and ACS' Alpha™ catheter (shown in U.S. Pat. No. 5,154,725), a hypotube forms the proximal outer tube of the catheter. This renders the catheter very pushable, at least at the proximal end. In the Express™ catheter, a spring coil immediately distal to the hypotube reinforces the lumen in the transition zone to minimize kinking, but does not provide the advantages of the spring coil to the distal tip of the catheter.

SUMMARY OF THE INVENTION

The present invention is a catheter avoiding many of the above-mentioned disadvantages. In some aspects, it provides a highly pushable catheter system, and a catheter system with a highly visible guidewire, a highly trackable biaxial lumen, and rapid exchange and/or perfusion capabilities.

Specifically, in one aspect, the invention is a catheter having an elongated shaft with a proximal and a distal end and defining a lumen, a therapy means such as a balloon having a distal and proximal end, the therapy means disposed at the distal end of the shaft, and a sleeve defining a second lumen, the sleeve extending proximally from the distal end of the catheter exterior to the balloon, for slidingly receiving a guidewire.

In the preferred embodiment, the sleeve terminates in a proximal port substantially distal of the proximal end of the shaft, but proximal of the balloon. The sleeve may be slit longitudinally for easy removal of the guidewire. In another embodiment, the sleeve includes apertures for drug delivery or perfusion and may extend to the proximal end of the catheter. The sleeve is preferably fixed adjacent the shaft.

In another aspect, the invention includes a catheter formed of an elongated shaft forming a lumen, the shaft formed of a proximal hypotube extending at least about half the length of the catheter, and a distal spring coil attached to the hypotube. Preferably, the catheter includes a therapy means such as a dilatation balloon affixed to its distal end, the above-mentioned sleeve forming an external wire lumen and other features mentioned above.

The invention in yet other aspects includes methods of using the above-mentioned inventions.

DETAILED DESCRIPTION OF THE PREFERRED EMBODIMENTS

Referring to FIGS. 1 through 8, a preferred rapid exchange catheter 5 according to the present invention is formed of a shaft 35, an external wire lumen 50 and a balloon 25. Shaft 35 comprises a stainless steel hypotube 90, usually Teflon™ coated, a spring coil 15, and a jacket 20 surrounding the coil. At the proximal end, a hub 65 is adhesively bonded to hypotube 90.

As shown in FIGS. 2–4 and 6, the spring coil 15 is brazed (at 85) to the distal end of hypotube 90 and extends to the proximal end of balloon 25. Spring coil 15 is a helically wound flat wire preferably made of a biocompatible material such as stainless steel or tungsten and, together with the hypotube, renders the catheter highly pushable. The hypotube extends at least about half the length of the shaft, preferably about three-quarters of the length of the shaft, and the spring coil forms the remainder of the shaft. In the preferred embodiment, the catheter is about 135 cm long and the hypotube extends through the proximal 109 centimeters. The spring coil is sealed and jacketed with polyethylene 20 or another conventional material so that it forms an inflation lumen 30.

In the preferred embodiment, jacket 20 covering spring coil 15 consists of a biocompatible material such as high or low density polyethylene or polyester. Jacket 20 is heat shrunk at its proximal end to the distal end of hypotube 90 and over the proximal end of spring coil 15. The inner diameter of jacket 20 is preferably 0.031 inches and the outer diameter is preferably 0.034 inches.

Balloon 25 is heat shrunk to the distal end of spring coil 15 and jacket 20. The balloon is preferably made of a non-compliant biocompatible material such as polyethylene and is in fluid communication with the inflation lumen 30 which is used to transmit fluids therethrough for purposes of inflating the balloon 25 and reducing the stenosis.

A core wire 10 is attached to hypotube 90 and extends through spring coil 15 and through balloon 75 to the distal end of the catheter. Core wire 10 is tapered in steps every 4 centimeters along its length, from a diameter of about 0.012 inches to about 0.003 inches. Core wire 10 provides stiffness which improves pushability and torquability, although in embodiments where the catheter materials are stiff enough to provide sufficient pushability alone (as may be the case with high density polyethylene or polyester), the core wire may be omitted (as in the catheter of FIGS. 11–15), and the catheter manufactured as a one-piece extrusion.

A radiopaque marker band 40 is bonded to core wire 10 preferably at the center of the balloon 25. The marker band 40 is used to fluoroscopically view the position of the balloon 25 during dilatation. Preferred materials for the marker band 40 include gold or platinum or iridium and alloys of these materials such as 90% platinum and 10% iridium. The distal portion of the spring coil 15 may also be fabricated of a radiopaque material such as platinum to make it visible under a fluoroscope. In some embodiments, the marker band 40 may be eliminated and the entire spring coil 15, or just the distal end of the spring coil 15, made of radiopaque materials as described above. The marker band 40 may also be placed at the center of the guidewire lumen 50 to easily allow the physician to accurately locate the balloon with respect to the shape or morphology of the lesion.

Figure 1:
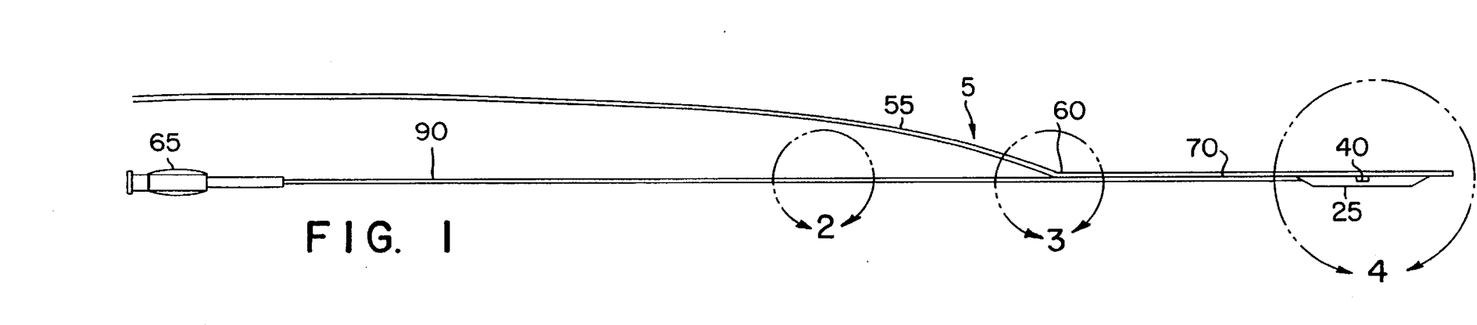
FIG. 1 represents the side elevational view of an embodiment of an angioplasty catheter incorporating the present invention.
Figure 2:
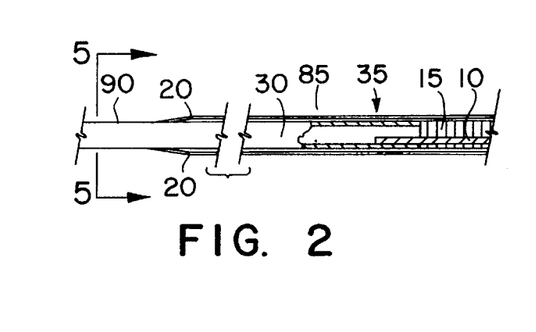
FIG. 2 represents the longitudinal cross-sectional view of area 2 of FIG. 1 where the hypotube attaches to the spring coil.
Figure 3:
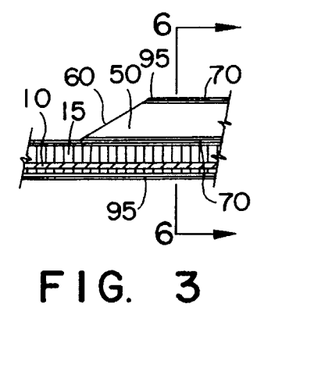
FIG. 3 represents the longitudinal cross-sectional view of area 3 of FIG. 1 where the wire sleeve attaches to the inflation lumen jacket.
Figure 4:
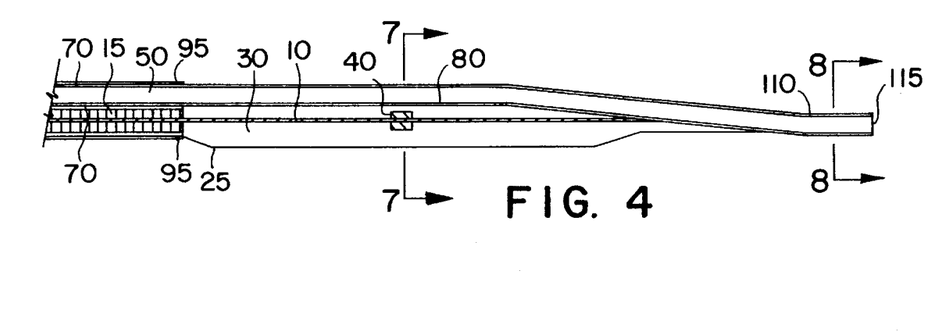
FIG. 4 represents the longitudinal cross-sectional view of area 4 of FIG. 1 at the balloon.
Figure 5:
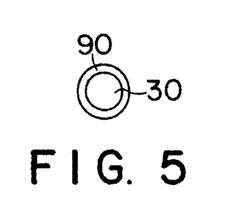
FIG. 5 represents the cross-sectional view of the catheter along the line 5—5 in FIG. 2.
Figure 6:
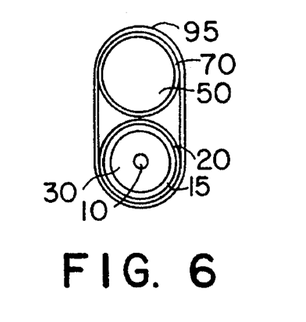
FIG. 6 represents the cross-sectional view as shown in FIG. 3 along the line 6—6.
Figure 7:
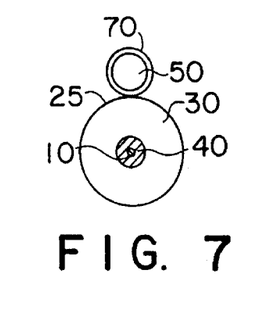
FIG. 7 represents the cross-sectional view of the sleeve and inflated balloon at the marker band as shown in FIG. 4 along the line 7—7.
Figure 8:
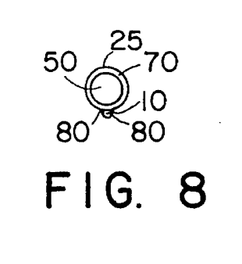
FIG. 8 represents the cross-sectional view of the catheter tip as shown in FIG. 4 along the line 8—8.

Extending generally parallel to the catheter and exterior to balloon 25 is external guidewire lumen 50 which is defined by sleeve 70. Sleeve 70 originates at the distal end of the catheter and forms the catheter tip 110. In the embodiment of FIG. 4, tip 110 is longer than a standard tip, approximately 3.5 mm long, to accommodate the sleeve 70. Sleeve 70 in all embodiments will slidably receive and direct guidewire 55 during use, the guidewire passing through proximal port 60, through the sleeve and through distal port 115.

Figure 16:
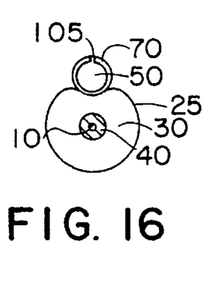
FIG. 16 represents the cross-sectional view of FIG. 12 along the line 15—15 with the notch plus inflated balloon embodiment.

When the catheter is used as a rapid exchange catheter, sleeve 70 is preferably either about 7 cm long or about 20 cm long, as shown in FIGS. 1–8, the shorter guidewire lumen promoting easy exchange of the catheter. In the preferred embodiment, the inner diameter of sleeve 70 is preferably about 0.017 inches (for a 0.014 inch guidewire), and the outer diameter is preferably about 0.021 inches. In another embodiment, the inner diameter may be about 0.013 inches (to fit a 0.010 inch guidewire), and the outer diameter about 0.018 inches. The sleeve can be made of high density polyethylene, polyimide, polyester or nylon, and is preferably polyethylene. The sleeve 70 may have a longitudinal notch 105 running along the length of the sleeve, as in FIG. 16, for ease of guidewire removal.

In the preferred embodiment, sleeve 70 is attached to shaft 35 proximal to the balloon by lamination. The laminate, preferably low or high density polyethylene, is heat shrunk around sleeve 70 and shaft 35 to form a jacket 95 with an inner diameter preferably of about 0.031 inches and an outer diameter preferably of about 0.034 inches. To reduce bowing of the external lumen in the balloon area and thus to reduce the catheter profile, the sleeve 70 may be joined to the balloon 25 with adhesive 80 which may be centered with respect to the balloon 25 or located at the ends of the balloon. The adhesive 80, if centered, can be applied to an area from about 3 mm to about 1 cm long.

Sleeve 70, balloon 25 and core wire 10 are joined at the distal end. In the preferred embodiment (see FIG. 8), balloon 25 is wrapped around sleeve 70 and heat shrunk into place. A Teflon™ coated mandril is placed within the sleeve during the process to maintain the shape and exit port. The core wire itself can be attached by adhesive to sleeve 70.

Using the catheter of FIGS. 1–8, a stenosis will be treated by first inserting a guiding catheter and then inserting a guidewire 55 and catheter 5 of the present invention over the guidewire to place the balloon within the stenosis. The balloon 25 of the catheter may then be inflated to dilate the stenosis. If a balloon of a different size is desired, catheter 5 can then easily be removed by sliding it along the guidewire while holding the guidewire in place in the vasculature, and another catheter back-loaded onto the wire and then positioned with the balloon in the stenosis for inflation.

Figure 9:
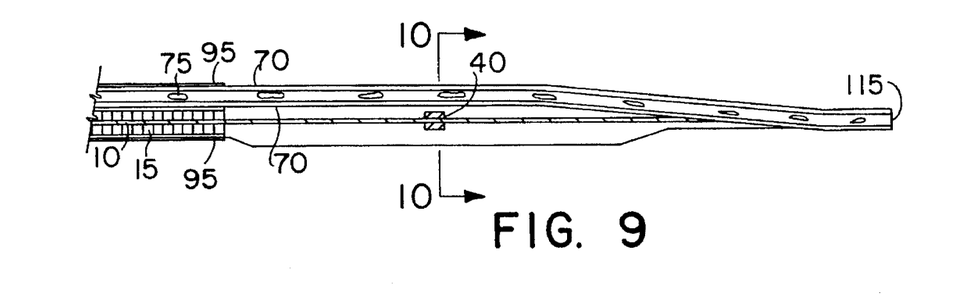
FIG. 9 represents the longitudinal cross-sectional view of the balloon segment in a perfusion catheter embodiment.
Figure 10:
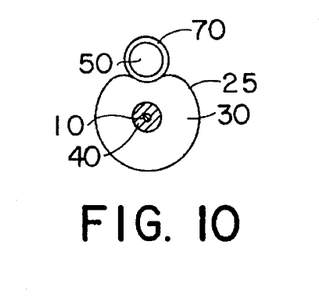
FIG. 10 represents the cross-sectional view along the line 10—10 of FIG. 9 at an inflated balloon marker band.
Figure 11:
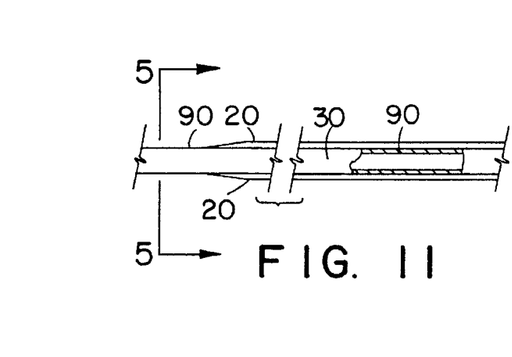
FIGS. 11–13 represent the longitudinal cross-sectional view of an embodiment without a core wire.
Figure 12:
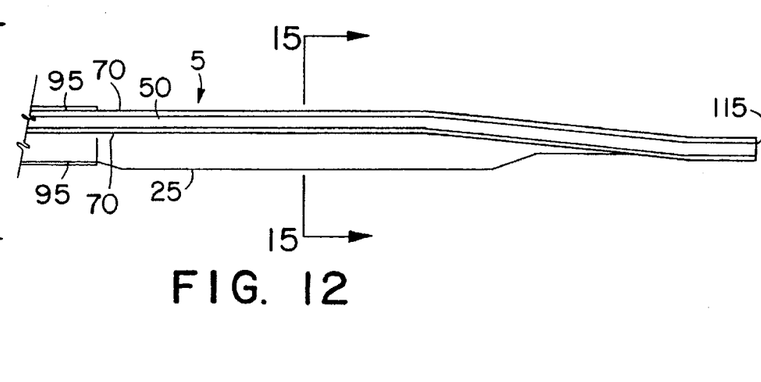
Figure 13:
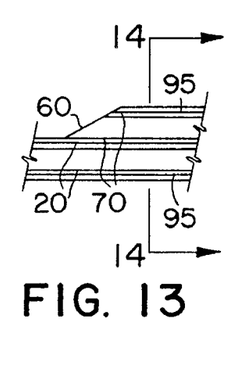
Figure 14:
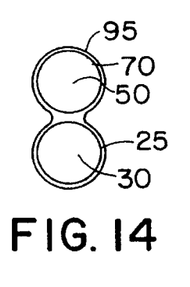
FIG. 14 represents the cross-sectional view of FIG. 13 along the line 14–14.
Figure 15:
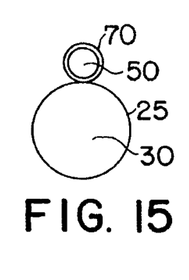
FIG. 15 represents the inflated balloon cross-sectional view of FIG. 12 along the line 15—15.
Figure 17:
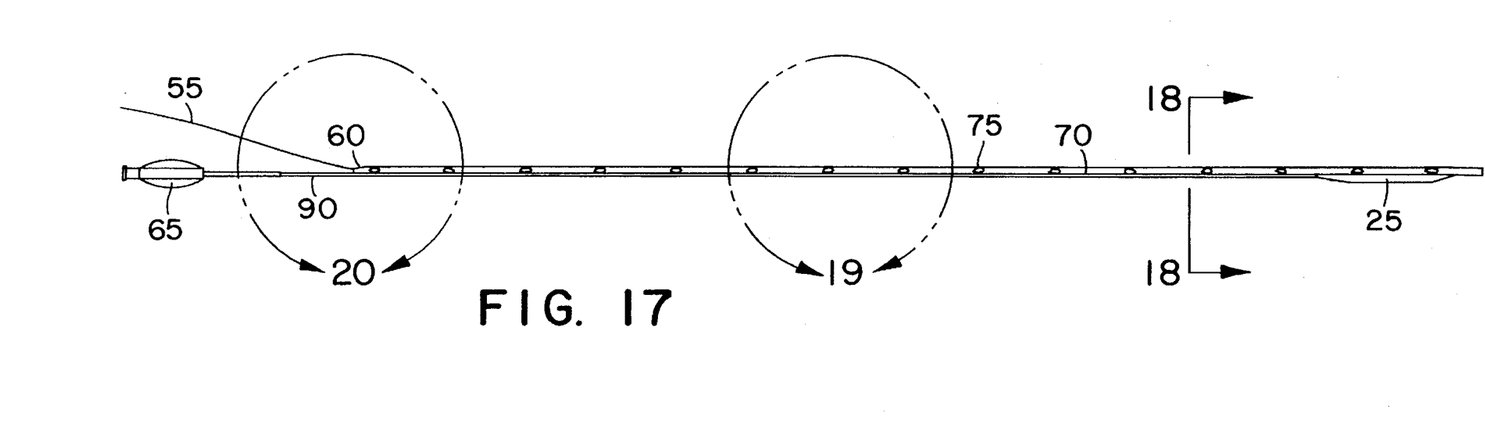
FIG. 17 represents the elevational view of an embodiment of an angioplasty catheter used in perfusion or drug delivery.
Figure 18:
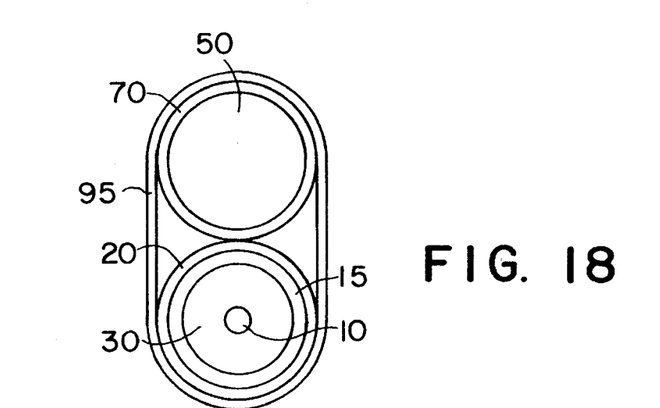
FIG. 18 represents the cross-sectional view of the catheter of FIG. 17 along the line 18—18 in FIG. 17.
Figure 19:
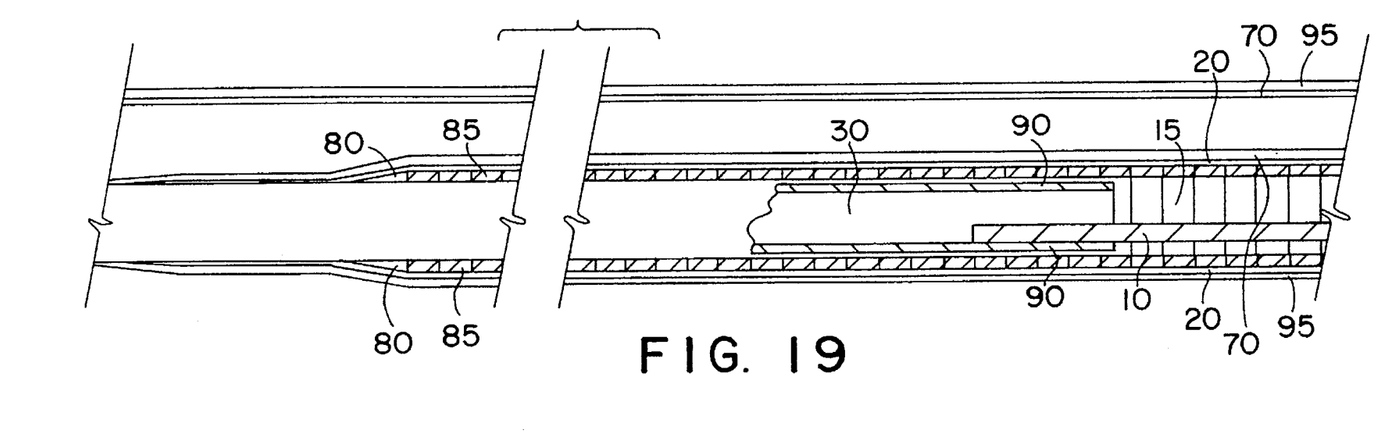
FIG. 19 represents the longitudinal cross sectional view of area 19 of FIG. 17.
Figure 20:
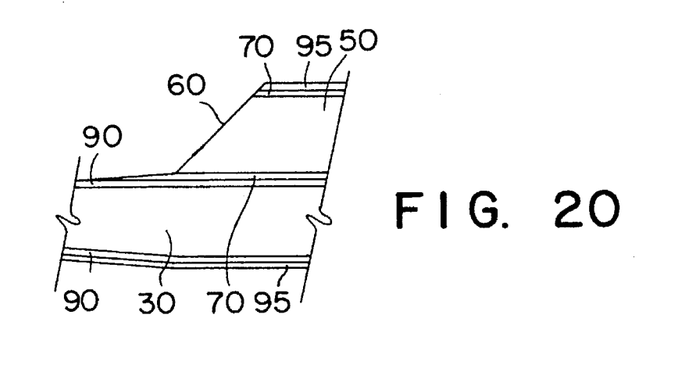
FIG. 20 represents the cross-sectional view of the catheter of FIG. 17 area 20.

Turning now to FIGS. 9 and 10, the distal end of an embodiment of the catheter of the present invention useful as an auto perfusion catheter is shown. In this embodiment of the invention, sleeve 70 contains apertures 75 useful as ports to enhance the passage of blood from the proximal to the distal end of the catheter. In addition, these ports can be used for perfusion or drug delivery. In such a case, the sleeve usually extends all the way to the proximal end of the catheter as in FIG. 17 so that fluid can be delivered into the external lumen defined by the sleeve.

From the foregoing detailed description of specific embodiments of the present invention, it should be apparent that a catheter, particularly, a rapid exchange catheter a drug delivery catheter and a perfusion catheter have been described. Although particular embodiments of the invention have been described herein in some detail, this has been done for the purposes of illustration only and is not intended to be limiting with respect to the scope of the invention. It has been contemplated by the inventors that various changes, alterations, or modifications may be made to the invention as described herein without departing from the spirit and scope of the invention as defined by the appended claims.

| No. | Component |
| --- | --- |
| 5 | Balloon Catheter |
| 10 | Core Wire |
| 15 | Spring Coil |
| 20 | Inflation Lumen Jacket |
| 25 | Balloon |
| 30 | Balloon Inflation Lumen |
| 35 | Shaft |
| 40 | Radiopaque Marker Band |
| 45 | Distal Tip |
| 50 | External Lumen |
| 55 | Guidewire |
| 60 | Exit Port |
| 65 | Handle |
| 70 | Sleeve |
| 75 | Perfusion Ports |
| 80 | Adhesive |
| 85 | Braze |
| 90 | Hypotube |
| 95 | External Lumen Jacket |
| 100 | Perfusion Lumen |
| 105 | Notch |
| 110 | Tip |
| 115 | Distal Port |

What is claimed is:

1. A catheter comprising:

an elongated shaft having a proximal and a distal end the shaft is comprised of a hypotube at its proximal end and a spring coil at its distal end, the shaft defining a lumen;

a balloon having a distal and proximal end, the balloon disposed at the distal end of the shaft and sealed thereto so that the balloon is in fluid communication with the lumen;

a sleeve defining a second lumen, the sleeve extending proximally from the distal end of the catheter exterior to the balloon, for slidably receiving a guidewire; and a core wire extending through the interior of the balloon from the distal end of the balloon to a point proximal to the balloon to provide added support to the catheter and to the balloon.

2. A catheter comprising:

an elongated shaft having a proximal and a distal end, the shaft is comprised of a hypotube, the shaft defining a lumen;

a balloon having a distal and proximal end, the balloon disposed at the distal end of the shaft and sealed thereto so that the balloon is in fluid communication with the lumen;

a sleeve defining a second lumen, the sleeve extending proximally from the distal end of the catheter exterior to the balloon, for slidingly receiving a guidewire; and a core wire extending through the interior of the balloon from the distal end of the balloon to a point proximal to the balloon to provide added support to the catheter and to the balloon.

3. A catheter comprising:

an elongated shaft having a proximal and a distal end, the shaft is comprised of a spring coil, the shaft defining a lumen:

a balloon having a distal and proximal end, the balloon disposed at the distal end of the shaft and sealed thereto so that the balloon is in fluid communication with the lumen;

a sleeve defining a second lumen, the sleeve extending proximally from the distal end of the catheter exterior to the balloon, for slidingly receiving a guidewire; and a core wire extending through the interior of the balloon from the distal end of the balloon to a point proximal to the balloon to provide added support to the catheter and to the balloon.

4. A catheter comprising:

an elongated shaft having a proximal and distal end, the shaft defining a lumen;

a balloon having a distal and proximal end, the balloon disposed at the distal end of the shaft and sealed thereto so that the balloon is in fluid communication with the lumen;

a sleeve defining a second lumen, the sleeve extending proximally from the distal end of the catheter exterior to the balloon, for slidingly receiving a guidewire, the sleeve being slit longitudinally for easy removal of the guidewire; and a core wire extending through the interior of the balloon from the distal end of the balloon to a point proximal to the balloon to provide added support to the catheter and to the balloon.

5. A catheter comprising:

an elongated shaft having a proximal and distal end, the shaft defining a lumen;

a balloon having a distal and proximal ends, the balloon disposed at the distal end of the shaft and sealed thereto so that the balloon is in fluid communication with the lumen;

a sleeve defining a second lumen, the sleeve extending proximally from the distal end of the catheter exterior to the balloon, for slidingly receiving a guidewire, the sleeve containing apertures for drug delivery or perfusion; and core wire extending through the interior of the balloon from the distal end of the balloon to a point proximal to the balloon to provide added support to the catheter and to the balloon.

* * * * *

UNITED STATES PATENT AND TRADEMARK OFFICE
CERTIFICATE OF CORRECTION

PATENT NO. : 5,549,556
DATED : August 27, 1996
INVENTOR(S) : Ndondo-lay et al.

It is certified that error appears in the above-indentified patent and that said Letters Patent is hereby corrected as shown below:

Col. 8, Line 20: "proximal ends," should be changed to "proximal end"

Col. 7, Line 24: "scaled thereto" should be changed to "sealed thereto"

Signed and Sealed this

Seventh Day of October, 1997

Attest:

BRUCE LEHMAN

Attesting Officer

Commissioner of Patents and Trademarks